United States Patent [19]
Killian et al.

[11] Patent Number: 5,876,387
[45] Date of Patent: Mar. 2, 1999

[54] DEVICE FOR THE CLOSURE OF WOUNDS AND SUCTIONING OF SECRETIONS THEREFROM

[75] Inventors: Frank Killian, Ebersberg, Germany; Michael O'Halloran; Oswald Picker, both of Vienna, Austria

[73] Assignee: Biovac Medizintechnik GmbH, Vienna, Austria

[21] Appl. No.: 704,590

[22] PCT Filed: Mar. 10, 1995

[86] PCT No.: PCT/EP95/00903

§ 371 Date: Jan. 6, 1997

§ 102(e) Date: Jan. 6, 1997

[87] PCT Pub. No.: WO95/24230

PCT Pub. Date: Sep. 14, 1995

[30] Foreign Application Priority Data

Mar. 10, 1994 [DE] Germany .......................... 94 04 048 U

[51] Int. Cl.⁶ ...................................................... A61M 1/00
[52] U.S. Cl. ............................................. 604/319; 604/320
[58] Field of Search ................................ 604/4, 317, 319, 604/320–323, 403, 408; 128/760; 137/205; 141/59

[56] References Cited

U.S. PATENT DOCUMENTS

| | | |
|---|---|---|
| 2,847,007 | 8/1958 | Fox . |
| 2,999,500 | 9/1961 | Schurer . |
| 3,848,628 | 11/1974 | Deaton et al. ........................... 604/317 |
| 4,111,204 | 9/1978 | Hessel ..................................... 604/317 |
| 4,275,732 | 6/1981 | Gereg ..................................... 604/317 |
| 4,306,557 | 12/1981 | North ..................................... 604/317 |
| 4,346,711 | 8/1982 | Agdanowski et al. .................. 604/317 |
| 4,430,084 | 2/1984 | Deaton ................................... 604/317 |
| 4,522,623 | 6/1985 | Laiterjiing .............................. 604/319 |
| 4,772,256 | 9/1988 | Lane et al. ................................. 604/4 |

FOREIGN PATENT DOCUMENTS

WO 84/02078  6/1984  WIPO .

*Primary Examiner*—John G. Weiss
*Assistant Examiner*—David J. Cho
*Attorney, Agent, or Firm*—Scully, Scott, Murphy & Presser

[57] ABSTRACT

The subject of the invention is a suction draw off device which permits a drawing off by suction of secretion, blood or the like and a closure of a wound by means of vacuum. Thereby, the suction draw off device has a container (1) closable by means of a lid (2), a bag (3) with a tube (4) which can be placed in the container (1), a passage for the tube in the upper part of the container wall or in the lid for drawing of the secretion or the like into the bag (3) and an opening in the container wall or in the lid for generating a vacuum in the container (3). Thereby, the suction draw off device is so configured that it is closed in a vacuum-tight manner in the closed condition of the container (1), so that the secretion suction draw off device is operable independently of a vacuum pump unit after a vacuum has once been generated in the container (1). For the case of the drawing off of blood during an operation, the bag (3) advantageously has a membrane (28) by means of which air drawn into the bag (3) in the container (1) can be released.

23 Claims, 3 Drawing Sheets

DEVICE FOR THE CLOSURE OF WOUNDS AND SUCTIONING OF SECRETIONS THEREFROM

BACKGROUND OF THE INVENTION

1. Field of the Invention

The present invention relates to a device for the closure of wounds by vacuum and/or for the drawing off by suction of secretions or the like, which is in particular suitable for use in fields of surgery in hospitals and in the medical services.

Devices for drawing off by suction of secretion, blood or the like and devices used for the closure of wounds after redon drainage are in use in many fields of medical treatment and health care. All systems to date are based upon the principle that an under-pressure is generated in a container, mostly a glass or plastics bottle, preferably transparent, by means of a vacuum. After Redon drainage an under-pressure is generated by means of a drain placed in the area of the wound in the zone of operation, which presses the wound surfaces against one another whereby hollow spaces—e.g. in the case of surgical removals—are avoided. Associated therewith at the same time is the transporting away (drawing off) of secretion. Upon drawing off by suction, secretion, e.g. from a freshly operated wound, is drawn off through a drain in the zone of operation into the container by means of the under-pressure. Continuous drawing off accelerates the healing process. With the use of suction draw off devices in the course of an operation, blood is drawn off into the container which blood is intended to be used after subsequent preparation for the purpose of self transfusion. Thus, the patient's own blood can be returned to the patient during or after an operation, which removes the danger of the transfer of an infectious agent, such as for example hepatitis viruses, HIV etc. Thereby, the disadvantage is that the tubes and the entire container for receiving the drawn off secretion or blood must be cleaned and newly sterilized after each use or must be completely disposed off as a disposable product.

2. Discussion of the Prior Art

In order to avoid this great outlay, there is proposed in DE-OS-25 36 746 the employment of disposable bags, e.g. of plastics, which are placed in the container. After placement of the bag in the container, the container is closed by means of a lid. A tube, usually connected in one piece with the bag, leads through a passage in the lid to the drain, i.e. to the zone of operation. A further opening in the base of the container is constantly connected with a vacuum pump. This vacuum pump generates in the container, through the continuous pumping off of air, a permanent under-pressure. In case of failure of the vacuum pump provision is made for switch over to or automatic response of a central suction facility of the hospital. This under-pressure has the effect that the bag in the container inflates to a certain extent. This inflation of the bag has, due to the increase in volume of the bag, in turn the consequence that an under-pressure is provided in the interior of the bag, so that the secretion is drawn off into the bag through the tube. When the bag is full the used tube and the full bag are simply removed and disposed of, and a new, sterile bag, and a new, sterile tube placed in the container. By these means first, even during storage, much space is saved since the bags take up less space than the rigid and non-collapsible containers. Secondly, the necessity to constantly clean and sterilize the containers is avoided.

The disadvantage with this prior art is that the vacuum pump generating the under-pressure in the container must be in constant operation, since otherwise the under-pressure in the container and thus the suction effect in the bag cannot be maintain. The need to connect this suction draw off device constantly to a continuously operated vacuum pump has many disadvantages. Thus, for example, for each suction draw off device there is needed a vacuum pump or a connection to a central suction facility. As an alternative thereto, there have already been proposed rigid containers, pre-evacuated by the manufacture, of glass or plastics, to be used as disposable containers, in particular for redon drainage applications. Here, storage, and also disposal, are extremely problematic and costly. Conventional devices for the closure of wounds by vacuum and/or for the drawing off of secretion are thus not usable, or of only very limited use, for ambulant treatment applications.

There is thus an acute need for a universally employable, easily manipulable device for the generation of an under-pressure in the region of a wound, suitable for ambulant treatment use, i.e. usable in any location.

SUMMARY OF THE INVENTION

This object is achieved by means of the features of claim 1 of the present invention.

Thereby, the primary aspect of the present invention lies in the configuration of the container to be so closable that a single pumping off of the container interior is sufficient to generate a suction effect in the bag which persists for a sufficiently long period of time. This means on the one hand that the lid must close the container in a vacuum-tight manner. On the other hand, also the opening through which the air is pumped off out of the container interior by means of the vacuum pump, must be closable in a vacuum-tight manner e.g. by means of a valve or the like. Further, and this is one of the most significant points of the invention, the passage of the tube for drawing off the secretion must be so configured that the tube can be placed in the container in a vacuum-tight manner. This is ensured by means of the special configuration of a sealing element attached to the tube, which sealing element can be easily and without problem inserted into the opening provided therefor and by means of which the tube can be passed through the lid or the container wall. By these means it is possible, with a single pumping off, to generate a sufficiently high and sufficiently enduring suction effect. The great advantage is thereby that the vacuum pump is separated after the pumping off of one container and can be employed for the pumping off of further containers. It is thus not necessary to provide a vacuum pump for each suction draw off device. The secretion suction draw off device in accordance with the present invention is thus universally, and also in ambulant treatment cases, employable.

With a view in particular to the drawing off of blood during an operation, for the purpose of later re-use, the bag may have a liquid-tight arrangement which is, however, air-permeable in one direction, for the removal of sucked in air from the bag. Thus, a more effective filling of the bag can be achieved. The bag filled with blood can then be directly employed for a blood re-transfusion.

BRIEF DESCRIPTION OF THE DRAWINGS

In the following, the invention will be described in more detail with reference to the accompanying drawings and with reference to exemplary embodiments. There is shown.

DETAILED DESCRIPTION OF PREFERRED EMBODIMENTS

Figure 1:
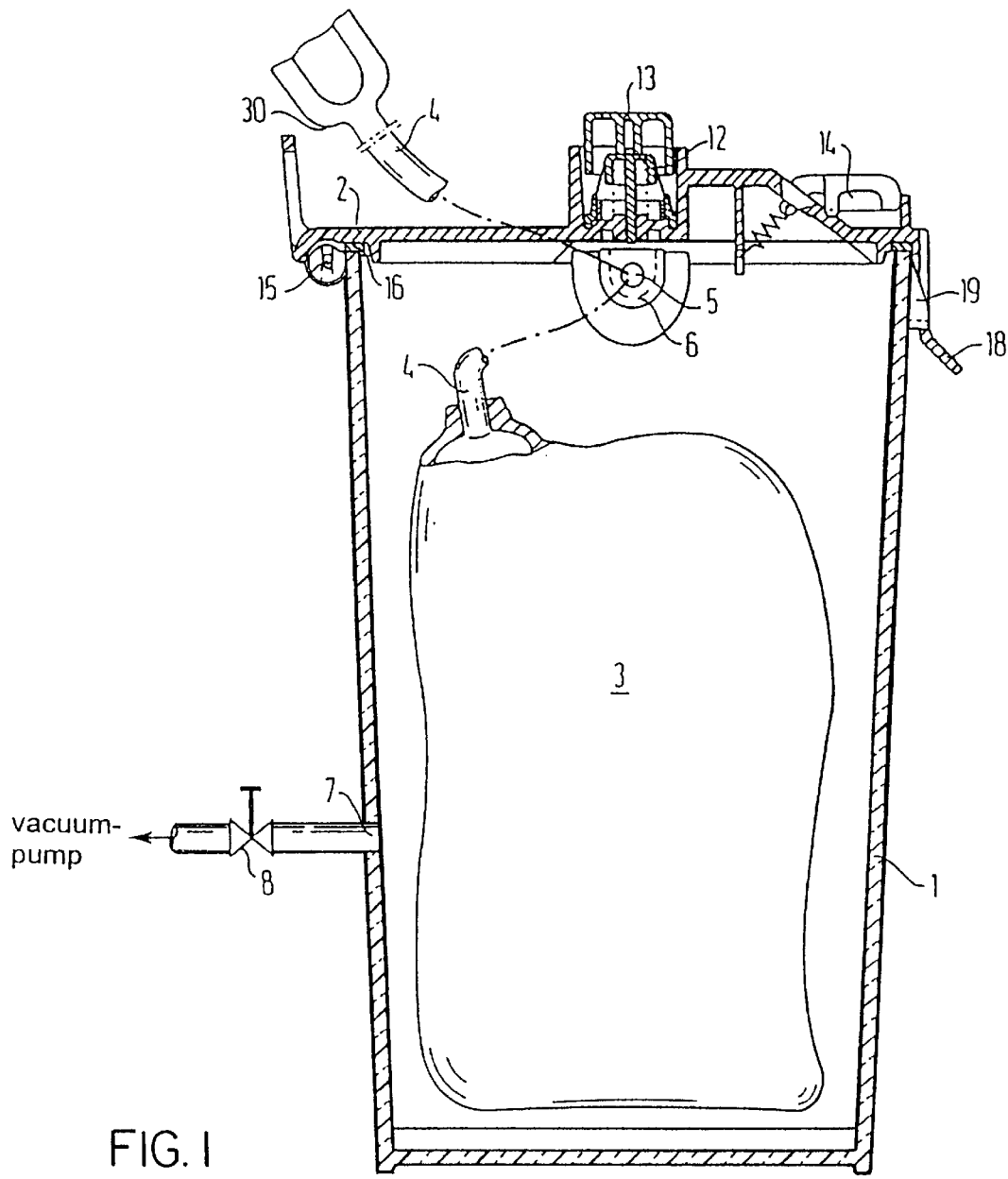
FIG. 1 a suction draw off device according to the present invention with closed container in which the bag and the tube having the sealing element are inserted.

FIG. 1 shows a container 1, which may be e.g. of glass or advantageously transparent plastics (e.g. acrylic glass). This container 1 can be closed in a vacuum-tight manner by means of a lid 2. A bag 3 is placed in the container, to which bag a tube 4 of sterilizable material, e.g. PVC, silicone or the like, is attached. The bag 3 serves for receiving the wound secretion, such as e.g. blood, pus or the like, drawn off by means of the tube 4 from a wound or the like. Bag 3 and tube 4 are preferably formed in one piece. The bag 3 and the tube 4 are further of air-impermeable material. In the emplaced condition, the tube 4 is led outwardly, out of the interior of the container 1, through an opening 5 by means of a sealing element 6. Thereby, the sealing element 6 is attached to the tube 4, e.g. by means of adhesive or the like. The sealing element 6 closes the opening 5 in a vacuum-tight manner at least when the lid 2 is closed. Preferably, and as shown, the opening 5 may be found in the upper part of the container wall, but also in the lid 2—in the sense of a kinematic reversal. A vacuum pump for pumping off the air out of the interior of the container 1 can be connected by means of a tube or the like to a further opening 7 in the container wall or in the lid 2. This is only schematically illustrated. This opening 7 is likewise sealable in the vacuum-tight manner with a valve 8. By means of the vacuum-tight configuration of the arrangement of sealing element 6, container 1, lid 2 and valve 8, a vacuum once generated by means of pumping off of air out of the interior of the container 1, is maintained for a very long period with closed lid 2 and with closed valve 8, at least for so long until the bag 3 is routinely removed either in dependence upon the degree of filling of the bag 3 or after a few hours. The vacuum in the interior of the container 1 has the consequence that the bag 3, put in place in the container 1 before the generation of the vacuum, inflates to a certain degree and at the end of the tube 4, formed in a manner of a probe, penetrating into the wound or into the secretion to be drawn off, a suction effect is produced.

The sealing element 6 is thereby inserted into the opening 5. If the bag 3 is filled with secretion, it can be easily and simply exchanged by means of opening of the lid 2, (if appropriate after opening of the valve 8) and by means of simple withdrawal of the seal 6 together with the tube 4 from the opening 5. The bag 3 with tube 4 and sealing element 6 is disposed off. A contamination of the container 1 has not taken place.

Figure 2:
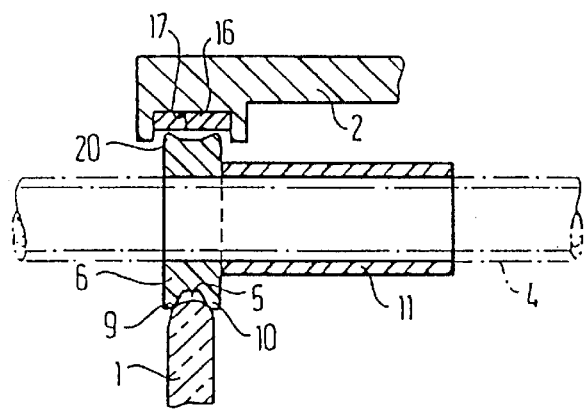
FIG. 2 an enlarged detail with the lid seal and the sealing element inserted into the side wall of the container.

FIG. 2 shows in section an enlarged detail of FIG. 1, with the sealing element 6 inserted into the opening 5 and the connection between container wall and lid 2 in detail. The sealing element 6 is in substance annular with respective (encircling) lips 9, 10 at the front and rear sides. These two lips 9 and 10 extend, on the entire circumference of the ring, radially outwardly. In the inserted condition of the sealing element 6, the edge of the container wall (or lid wall) defining the opening 5 is clamped between these two lips, as is to be seen in FIG. 2. The function of the two lips is thus, on the one hand to hold the sealing element 6 in the opening 5 and on the other hand to close the opening in vacuum-tight manner. In a preferred configuration, the sealing element 6 may have at least on one side a pipe-like extension 11 which in the inserted condition of the sealing element 6 projects into the container interior. By these means there is prevented a bending off or damaging of the tube 4 led out of the container interior to the outside through the sealing element 6, or a loosening of the fixed connection between tube 4 and sealing element 6.

The container 1 is closed in a vacuum-tight manner by means of the lid 2, in that the upper edge of the container 1 e.g. engages into a circumferential recess or groove 17 at the edge of the lid 2. Thereby, a sealing ring 16 also arranged between the upper edge of the container 1 and the lid 2 can additionally provide for a reliable sealing off.

As explained, the fixed connection between the tube 4 and the sealing element 6, or its pipe-like extension 11, is of significance. It is possible to produce the sealing element 6 with pipe-like extension 11, in a sense as reinforcement of the tube 4, in one piece with the tube 4, but this is extremely problematic for technical and cost reasons. It is therefore expedient to use for the tube 4 materials conventional in medical technology and to manufacture the sealing element 6 with extension 11 of a thermoplastics such as an SBS plastics consisting of a thermoplastic elastomeric styrene block copolymer (for example of a mold mass obtainable under the registered trademark KRATON of the firm Shell) and to connect this with the tube 4 in one piece. This may be effected by means of gluing with an adhesive or by means of dissolving together the surfaces of tube 4 and sealing element 6, or pipe-extension 11, to be connected together. If the sealing element is of a natural rubber such as latex, although it cannot be glued to the tube 4, the sealing and fixed connection is then achieved by means of an elastic tensioning which is exercised by the sealing element 6 and the extension 11 on the tube 4.

Decisive for the choice of material, and also of the adhesive, is that the materials on the one hand are permanently vacuum-tight and on the other hand that the materials are not affected, in particular not destroyed, even with the usual sterilization.

As further illustrated in FIG. 1, it is expedient to provide the suction draw off device with additional elements, which are preferably arranged in the lid 2, namely on the one hand an indicator element which on the one hand shows the build up of the vacuum within the container 1 and on the other hand however shows also when the gradually occurring removal of the vacuum has reached an extent such that the suction working can no longer be ensured. Here, it is expedient to arrange in the lid 2 a cap 13, configured with at least two colours, controlled by means of a spring-loaded membrane 12. The membrane 12—sealingly bonded or clamped in—takes up in the case of a high vacuum a lower lying position in which the cap 13 is also drawn downwardly. With reducing vacuum, the membrane 12 is pressed outwardly and thereby presses the cap 13 also upwardly, so that a visible indication is possible. Further, it is expedient to configure either the valve 8 itself so that it can be quickly opened for the release of the vacuum within the container 1 or to additionally provide an air entry valve 14 which can be quickly opened, such as a spring-loaded closure stopper which can be lifted out of its seating by means of a lever movement.

It is further expedient to apply the lid 2 to the container 1 by means of a hinge 15 fixedly but pivotably, and it is expedient to provide a hook-like or bracket-like locking element 18 on the lid, which can engage over a nose 16 of the container and thereby loads the sealing ring 16 in the circumferential groove 17.

Advantageously, the contours of the opening 5 and the sealing element 6 are substantially U-shaped in appearance in order to be able to introduce the sealing element 6, with the two lips 9 and 10 in a simple manner—with the lid 2 opened—from above into the opening 5. The edge defining the opening 5 may thereby the rounded, seen in section, in order to facilitate the abutment of the lips 9 and 10 with the sealing element 6 inserted.

In the event that several wounds of a patient are to be drained off by suction and/or closed, a plurality of drainage catheters may be led to the single tube 4 by means of a T-piece. As indicated in FIG. 1, this bringing together is effected advantageously outside the passage 5 of the container 3, so that a treatment of several wounds of the patient is made possible with only a single passage.

Figure 3A:
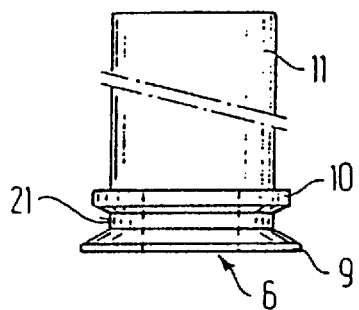
FIGS. 3a, 3b and 3c are, respectively, plan, side and longitudinal sectional views of the sealing element.
Figure 3B:
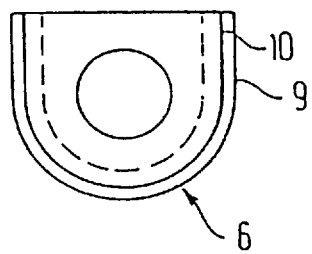
Figure 3C:
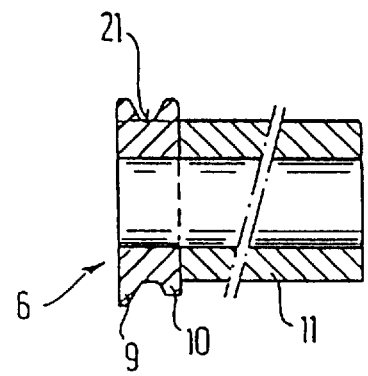

The sealing element 6 is shown again in detail in FIGS. 3a, 3b and 3c, in respectively plan, side and sectional views. The degree of vacuum sealing of the sealing element 6 is an important factor for the operation of the suction draw off device in accordance with the invention independently of a vacuum suction device. As is shown in FIG. 3, the sealing element 6 has a pipe-like extension 11 which, in the inserted condition, projects into the container interior. This pipe-like extension 11 hinders a bending of the tube 4 in the region of the container opening 5. Further, a twisted or oblique positioning of the tube 4 within the sealing element 6 is prevented in that the pipe-like extension 11 has the effect that in the region of the sealing element 6 tube 4 substantially always lies perpendicularly to the container wall.

The fixed connection of the tube 4 with both sealing element 6 and also extension 11 prevents a loosening of this connection by bending or folding of the tube 4 outside the container 1 when it is emplaced in the container.

As is illustrated in FIG. 2, the sealing element 6 has a double lip 20 on the side which—upon closing of the lid 2—is pressed by the lid. This double lip 20 is advantageously pressed by a sealing ring 16 of the lid 2 upon the closure movement. With the configuration illustrated in FIGS 3a, 3b and 3c, the sealing element 6 has a double lip 9, 10 only in the region in which the sealing element 6 engages into the edge defining the opening 5. As indicated in the sectional view, the double lip can also be formed completely around the circumference of the sealing element 6.

In the region between the two lips 9, 10, the circumference of the sealing element 6 may be rounded, or substantially parallel to the axis of the sealing element 6, when viewed transversely to the sealing element 6. Thereby, there is attained a particularly advantageous co-operation with the edge of the container defining the opening 5. For secure clamping of the sealing element 6 in the edge of the container defining the opening 5, the outer lip 9 can, in the inserted condition, have a larger diameter than the inner lip 10.

At least one of the two lips 9, 10 may be rounded or run out flat, in side view, in order to avoid the risk of damage to the lip which is increased with a lip which comes to a point.

Figure 4:
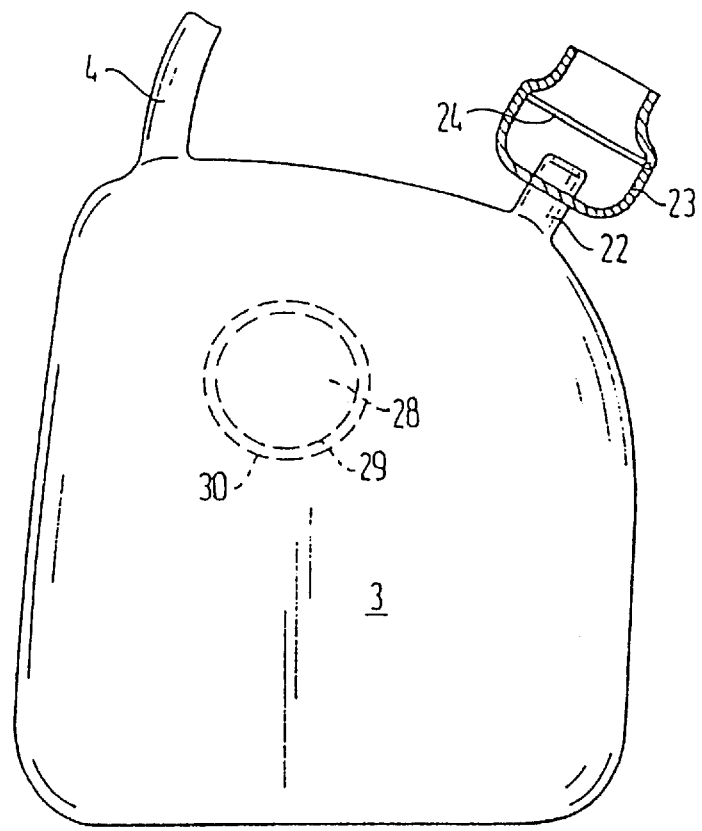
FIG. 4 a further exemplary embodiment for a bag such as can be employed in the suction draw off device in accordance with the invention.

FIG. 4 shows a configuration of the bag 3 such as is advantageous in particular for use of the suction draw off device in the course of an operation. With this application, during an operation, blood is drawn off from at least one wound of a patient into the bag 4 of the container 3. Thereby, the bag 3 has advantageously a volume of for example 500 ml, such as is usual for blood transfusion bags. Since, in this application of the suction draw off device in accordance with the invention, often a certain proportion of air is also drawn in, it is of advantage for the efficient filing of the bag 4 if the bag has an arrangement for the removal of drawn-in air from the bag 4 in the interior of the container 1. As illustrated, this can be effected for example by means of an applied connecting piece 22, to which there is applied a firm carrier 23, which mounts an air permeable but liquid-tight membrane 24. It is of great advantage if this membrane 24 prevents moisture or even organisms from leaving the container 3 through the opening piece 22 and the air passing through the membrane 24 thus experiences a certain sterilization. This can be provided for example by means of a membrane having micropores, as is for example commercially obtainable under the registered trademark GORE-TEX. Alternatively, such a membrane 28 may form a part of the wall of the bag 3. The membrane 28 may for example be moulded (30) at the edge into a cut-out 29 of the bag 3.

Figure 5:
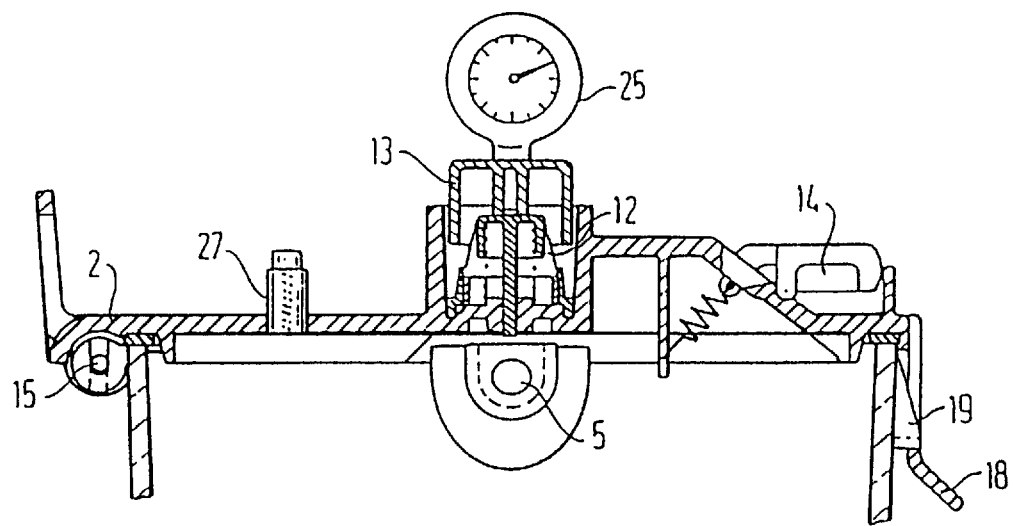
FIG. 5 a detailed view of the lid construction of the container.

FIG. 5 shows in detail the lid 2 of the container 1 of the suction draw off device in accordance with the invention. With reference to FIG. 1 it has already been described that by means of a spring-loaded membrane 12 and a cap 13, for example configured in two colours, a visual indication for the vacuum in the container 1 can be formed. For an exact checking of the vacuum in the container 1 there may be provided for indicating the vacuum also a digital or analog indicator device 25 of the vacuum, as represented in FIG. 5. Also, the cap 13 may be provided with a corresponding scale (not shown).

As further shown in FIG. 5, there may be provided in the lid 2 or in the wall of the container 1 a manually operable valve device 27 which allows a minimum interior pressure to be set for the container 2. With a automatically functioning valve device 27, in the manner of a safety valve (over-pressure valve) a particular limit value for the internal pressure can be determined. Of course, the air inlet valve 14 may alternatively be dimensioned and formed in a suitable manner, although with the exemplary embodiment it serves for rapid relief. With this, the container 2 can be easily and quickly evacuated at a pump station without there being a danger of generation of a too low internal pressure in the container 2, which might have as a consequence an adverse effect or even damage to the container 2. Expediently, but not shown in detail, there are provided security means which prevent a manipulation in particular of the elements which provide the sealing by unauthorised persons.

In summary, there is thus provided a suction draw off device with a disposable bag having a connected disposable tube which can be placed in the device, with which it is in operation merely necessary once to build up a vacuum, without it being necessary to maintain permanent connection of a vacuum pump. The suction draw off device in accordance with the invention is therefore suitable in particular for is ambulant treatment use and can also be used by patients who are not bedridden, and may be taken long by these patients. Thereby it is decisive that the vacuum can be maintained for so long until the bag is normally, i.e. routinely exchanged.

We claim:

1. A secretion suction draw off device employable in ambulant treatment, said device including a container (1); a lid (2) for vacuum-tightly closing said container; an impermeable and vacuum-tight bag (3) having a tube (4) which is insertable into the container (1), a first opening (7) in the wall of the container (1) via which a vacuum can be produced in the container (1) and which is sealed a vacuum-tightly by a valve (8), said the sealed container (1) being separable from a source producing the vacuum subsequent to generation of the vacuum, and a passage leading outside the device for the tube (4) for drawing off secretion into the bag (3) responsive to the vacuum generated in the sealed container (1), characterized in that the passage is formed by a second opening (5) selectively formed in an upper part of the container wall or in the lid (2); and an independent sealing element (6) fixedly connected to the tube which, upon the container (1) being open, is insertable into the second opening (5) such that, upon the lid (2) being moved to close the container (1), said container (1) and sealing element (6), at the end of a closing movement of the lid in essentially a direction which extends perpendicular to a longitudinal axis of the sealing element (6), and whereby said sealing element (6) is brought into abutment with the lid (2), and which includes a pipe-like extension (11) projecting into the interior of the container when in an inserted position therein.

2. The suction draw off device according to claim 1, characterized in that, the lid (2) has a sealing ring (16) which is pressed against the sealing element (6) when the lid (2) is closed.

3. The suction draw off device according to claim 1, characterized in that, the sealing element (6) has a pipe-like extension (11) which in the inserted condition projects into the container interior.

4. The suction draw off device according to claim 1, characterized in that, the tube (4) is fixedly attached with the sealing element (6) by being glued or welded.

5. The suction draw off device according to claim 1, characterized in that, the tube is of sterilizable polyvinylchloride material.

6. The suction draw off device according to 1, characterized in that, the sealing element (6) is of a sterilizable thermoplastic SBS plastics material.

7. The suction draw off device according to claim 1, characterized in that, the sealing element (6) is manufactured of a natural latex rubber.

8. The suction draw off device according to claim 1, characterized in that, the sealing element (6) has at a side facing towards the lid (2), a double lip (20) which upon the closure movement of the lid (2) is pressed against by the lid a vacuum-tight manner.

9. The suction draw off device according to claim 1, characterized in that, the sealing element (6) has a double lip (9, 10) into which, in the inserted condition, the edge defining the opening (5) can be clamped.

10. The suction draw off device according to claim 1, characterized in that, the sealing element (6) has a circumferential double lip (9, 10).

11. The suction draw off device according to any of claims 8 to 10, characterized in that, that the circumference of the sealing element (6), in the region between the double lips (9, 10; 20), viewed transversely to the sealing element (6), is selectively rounded or is in substance parallel to the axis of the sealing element (6).

12. The suction draw off device according to claim 11, characterized in that, the double lip and pipe-like extension (11) are in one piece with the sealing element (6).

13. The suction draw off device according to claim 11, characterized in that, the lip (9) of the sealing element (6) which is outermost in the emplaced condition has a greater diameter than the inner lip.

14. The suction draw off device according to claim 1, characterized in that, the device includes an indicator device for indicating the internal pressure of the container (1).

15. The suction draw off device according to claim 1, characterized in that, it has a device for indicating that a predetermined value of the internal pressure in the container (2) has been exceeded or dropped below specified boundaries.

16. The suction draw off device according to claim 1, characterized in that, it has a device for setting the minimum internal pressure of the container (1).

17. The suction draw off device according to claim 1, characterized in that, at least two tubes comprising drainage catheters on the suction draw off side are brought together by means of a vacuum-tight T-piece connected to the one tube (4).

18. The suction draw off device according to claim 17, characterized in that, the at least two suction draw off side tubes are brought together to the one tube (4) outside of the container (1).

19. The suction draw off device according to claim 1, characterized in that, the bag (3) has the tube (4) as a sole opening, and is otherwise sealed in a vacuum-tight manner with regard to the interior of the container (1).

20. The suction draw off device according to claim 1, characterized in that, the bag (3) has further an arrangement (22, 23, 24; 28, 29, 30) for the removal of drawn-in air from the bag (3) in the interior of the container (1), which arrangement is liquid-tight but air permeable in one flow direction.

21. The suction draw off device according to claim 20, characterized by a mounted membrane (24; 28).

22. The suction draw off device according to claim 21, characterized in that, the membrane (24) is placed in a stiff mount (23) which is attached to a tube connection (22) leading into the bag (3).

23. The suction draw off device according to claim 21, characterized in that, the membrane (28) is welded (30) into a cut-out (29) of the bag.

* * * * *